United States Patent [19]

Stevenson et al.

[11] Patent Number: 4,820,699
[45] Date of Patent: Apr. 11, 1989

[54] NOVEL BACTERICIDAL USE

[75] Inventors: Walter R. Stevenson; Arthur Kelman, both of Madison, Wis.

[73] Assignee: Sandoz, Ltd., Switzerland

[21] Appl. No.: 230,695

[22] Filed: Aug. 5, 1988

Related U.S. Application Data

[63] Continuation of Ser. No. 107,330, Oct. 13, 1987, abandoned.

[51] Int. Cl.⁴ ............................................. A01N 57/10
[52] U.S. Cl. ..................................................... 514/147
[58] Field of Search ......................................... 514/147

[56] References Cited

U.S. PATENT DOCUMENTS 4,006,229  2/1977  Drabek ................................. 514/147
4,039,635  8/1977  Kato et al. ........................... 514/147

FOREIGN PATENT DOCUMENTS 1179041  1/1970  United Kingdom ................ 514/147

Primary Examiner—Allen J. Robinson
Attorney, Agent, or Firm—Townsend & Townsend

[57] ABSTRACT

A new use of the fungicide O-(2,6-dichloro-4-methylphenyl) O,O-dimethyl phosphorothioate for the control of bacterial infection.

2 Claims, No Drawings

NOVEL BACTERICIDAL USE

This is a continuation of Ser. No. 07/107,330, filed Oct. 13, 1987.

The present invention relates to a new use of the fungicide O-(2,6-dichloro-4-methylphenyl) O,O-dimethyl phosphorothioate, which is also known by the common name tolclofos-methyl.

More particularly, this invention provides the use of tolclofos-methyl for the control of bacterial infection.

Tolclofos-methyl, which is disclosed in U.S. Pat. No. 4,039,635, has previously been used for controlling soil borne fungal diseases.

It has now surprisingly been found that tolclofos-methyl is useful for the control of bacteria, particularly bacteria harmful to agricultural plants. This compound can be an effective control agent for bacteria of, for example, the families Enterobacteriaceae and Pseudomonadaceae.

The invention accordingly comprises the use of tolclofos-methyl for bacterial control, comprising applying to the bacteria or their habitat a bacteria-controlling amount of tolclofos-methyl. The amount of compound to be applied will vary, depending on the mode and conditions of application, the particular bacterial pest involved, the crop to be treated and the like. Appropriate application rates can be determined by routine procedures by those skilled in the art.

In actual application of tolclofos-methyl for combatting bacteria, tolclofos-methyl may be used as it is or it can conveniently be employed as a bactericidal composition in association with acceptable diluent(s) for application to the bacteria or their habitat. Such compositions also form part of the present invention.

Suitable formulations contain from 0.01 to 99% by weight of active ingredient, from 0 to 20% of surfactant and from 1 to 99.99% of solid or liquid diluent(s). Higher ratios of surfactant to active ingredient are sometimes desirable and are achieved by incorporation into the formulation or by tank mixing. Application forms of a composition generally contain between 0.01 and 60% by weight of active ingredient. Lower or higher levels of active ingredient can, of course, be present depending on the intended use, the physical properties of the compound and the mode of application. Concentrate forms of a composition intended to be diluted before use generally contain between 2 and 90%, preferably between 5 and 80% by weight of active ingredient.

Useful formulations of tolclofos-methyl include dusts, granules, emulsifiable concentrates, wettable powders, flowables and the like. They are obtained by conventional manner, e.g. by mixing the compound with the diluent(s) and optionally with other ingredients.

Agriculturally acceptable additives may be employed in the bactericidal composition to improve the performance of the active ingredient and to reduce foaming, caking and corrosion, for example.

"Surfactant" as used herein means an agriculturally acceptable material which imparts emulsifiability, spreading, wetting, dispersibility or other surface-modifying properties. Examples of surfactants are sodium lignin sulfonate and lauryl sulfate.

"Diluent" as used herein means a liquid or solid agriculturally acceptable material used to dilute a concentrated material to a usable or desirable strength. For dusts or granules it can be e.g. talc, kaolin or diatomaceous earth, for liquid concentrate forms for example a hydrocarbon such as xylene or an alcohol such as isopropanol, and for liquid application forms i.e. water or diesel oil.

The compositions of this invention can also comprise tolclofos-methyl in a mixture with other compounds having biological activity, e.g. fungicides, insecticides, nematicides, herbicides and fertilizers, and the resulting compositions can greatly contribute to the simultaneous control of diseases and injurious insects and to the promotion of growth of crops.

The following examples are provided to illustrate the practice of the present invention.

EXAMPLE 1

Seedpieces (ca. 2 oz. each) of potato (*Solanum tuberosum* "Monona") are treated with fungicide immediately after cutting by uniformly coating with a fungicide dust. Two groups of 10 seedpieces from each treatment are placed in a mist chamber, where they are exposed to continuous mist for 72 hrs at 24° C. Each seedpiece is then evaluated for the extent of decay from bacterial soft rot (Erwinia spp.). The evaluation was repeated one week after the first evaluation. As is demonstrated by the results presented in Table A, treatment that includes tolclofos-methyl greatly reduces the severity of bacterial soft rot as compared to other fungicides tested, either alone or in combination, and to the untreated control.

TABLE A

| Treatment | oz a.i./cwt* | % Bacterial Soft Rot |
|---|---|---|
| untreated control | — | 11.5 |
| calcium sulfate | 16.0 | 94.9 |
| captan | 1.20 | 41.3 |
| thiophanate | 0.40 | 52.8 |
| thiophanate + iprodione | 0.40 + 0.16 | 36.7 |
| thiophanate + carboxin | 0.40 + 0.16 | 43.7 |
| thiophanate + tolclofos-methyl | 0.40 + 0.16 | 6.6 |

"cwt" is a term of art which means "100 pounds of seedpieces".

Captan is the common name for the fungicide, 1,2,3,6-tetrahydro-N-(trichloromethylthio)phthalimide.

Thiophanate is the common name for the fungicide, 1,2-di-(3-ethoxycarbonyl-2-thioureido)benzene.

Iprodione is the common name for the fungicide, 3-(3,5-dichlorophenyl)-N-isopropyl-2,4-dioxoimidazoline-1-carboxamide.

Carboxin is the common name for the fungicide, 5,6-dihydro-2-methyl-1,4-oxathi-ine-3-carboxanilide.

EXAMPLE 2

Seeds of cabbage which are infected with black rot (*Xanthomonas campestris*) are treated with tolclofos-methyl in a dust formulation and are then planted in a crisper box (ca. 3000 seeds/box) at 25°–30° C. High humidity is maintained for 2 weeks. The seedlings are observed for initial infection with the bacteria and for spread of the infection at the end of the 2 weeks. Initial infected seeds are observed as a site of dying seedlings. Without treatment, the pathogen spreads rapidly to eventually infect all seedlings in the test box. The results of the test are presented in Table B below. Tolclofos-methyl greatly reduces the incidence of initial infection and controls postemergent infections.

TABLE B

| Treatment | Initial Infection | 2 Weeks Post Treatment |
|---|---|---|
| untreated control | 10 sites/box | 100% dead |
| tolclofos-methyl | | |
| 2 oz a.i./cwt* | 4 sites/box | very slow spread |
| 4 oz a.i./cwt* | 2 sites/box | no spread - cannot reisolate *X. campestris* from dead sites |

*"cwt" is a term of art which means "100 pounds of seed".

EXAMPLE 3

Following the procedure of Example 2, seeds of non-infected cabbage are treated with tolclofos-methyl (8 oz. a.i./cwt) and planted. Untreated non-infected seeds are planted as a control. One week after planting, 0.5 ml of a suspension containing $10^9$ of *Xanthomonas campestris* ("Xcc") cells is added to each of three widely separated, marked locations in each of the treated and untreated boxes. Two weeks later, the area of infected seedlings is measured. The results in Table C show that seed treatment with tolclofos-methyl slows the spread of black rot.

TABLE C

| | Avg. Diameter of diseased area (mean dia. ± SD) |
|---|---|
| untreated control | 7.4 ± 5.5 cm. |
| treated | 1.2 ± 0.9 cm. |

EXAMPLE 4

Cabbage seeds infected with Xcc are soaked overnight in a 1:10 dilution of tolclofos-methyl, after which they are washed thoroughly and assayed for level of infection by the following seed-soaking assay procedure. Non-treated infected seeds are assayed in the same manner as a control.

Seeds are soaked in water at 30° C. for 6 hr with shaking, after which appropriate dilutions of the resulting liquid are plated on a semi-selective medium. Colonies that are similar to the pathogen in appearance are presumed to be Xcc. Their identity is then verified by development of characteristic symptoms after inoculation onto a susceptible host plant. The following results were obtained.

TABLE D

| | Xcc colonies/ml of seed washing |
|---|---|
| untreated control | $5 \times 10^3$ |
| treated | 0 |

What is claimed is:

1. A method for controlling bacterial infection which comprises applying to the bacteria a bacteria-controlling amount of O-(2,6-dichloro-4-methylphenyl) O,O-dimethyl phosphorothioate.

2. A method for controlling bacterial infection according to claim 1 wherein the bacteria are of the family Enterbacoteriaceae or Pseudomonadaceae.

* * * * *